US008100911B2

(12) United States Patent
Yamazaki et al.

(10) Patent No.: US 8,100,911 B2
(45) Date of Patent: Jan. 24, 2012

(54) FRACTURE FIXATION APPARATUS

(75) Inventors: Ken Yamazaki, Yokohama (JP);
Andrew H. Berthusen, Warsaw, IN (US); Anthony J. Metzinger, Winona Lake, IN (US); Charles D. Christie, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 763 days.

(21) Appl. No.: 12/164,475

(22) Filed: Jun. 30, 2008

(65) Prior Publication Data
US 2009/0326534 A1 Dec. 31, 2009

(51) Int. Cl.
*A61B 17/56* (2006.01)
*A61B 17/04* (2006.01)

(52) U.S. Cl. ............... 606/65; 606/62; 606/64; 606/301

(58) Field of Classification Search ............... 606/62–68, 606/280, 301, 286, 282, 329, 300, 232
See application file for complete search history.

(56) References Cited

U.S. PATENT DOCUMENTS

| 5,032,125 | A | 7/1991 | Durham et al. | |
|---|---|---|---|---|
| 5,041,116 | A | 8/1991 | Wilson | |
| 5,176,681 | A | 1/1993 | Lawes et al. | |
| 5,454,813 | A | 10/1995 | Lawes | |
| 5,562,666 | A | 10/1996 | Brumfield | |
| 5,713,902 | A | 2/1998 | Friedl | |
| 6,228,086 | B1 | 5/2001 | Wahl et al. | |
| 6,235,031 | B1 * | 5/2001 | Hodgeman et al. | 606/64 |
| 6,423,066 | B1 * | 7/2002 | Harder et al. | 606/65 |
| 6,443,954 | B1 * | 9/2002 | Bramlet et al. | 606/62 |
| 7,527,627 | B2 * | 5/2009 | Ferrante et al. | 606/64 |
| 2002/0032445 | A1 * | 3/2002 | Fujiwara | 606/67 |
| 2003/0004514 | A1 | 1/2003 | Frigg et al. | |
| 2005/0055024 | A1 | 3/2005 | James et al. | |
| 2005/0149025 | A1 | 7/2005 | Ferrante et al. | |
| 2008/0119856 | A1 | 5/2008 | Gotfried | |

FOREIGN PATENT DOCUMENTS

| EP | 1175872 A2 | 1/2002 |
|---|---|---|
| EP | 0 968 685 B1 | 9/2004 |
| WO | 03028567 A1 | 4/2003 |

OTHER PUBLICATIONS

PCT Search Report for PCT/US2009/047622, mailed on Sep. 1, 2009.
Stryker, "Gamma3 tm—The Compact Titanium Version of the Gamma tm Nail System", 2005, US.

* cited by examiner

*Primary Examiner* — Pedro Philogene
(74) *Attorney, Agent, or Firm* — Maginot, Moore & Beck

(57) ABSTRACT

An apparatus for treating a bone fracture comprises an intramedullary rod extending through a first bone segment of a fractured bone. A lag screw assembly extends through a first transverse aperture in the rod, while a control member extends through a second transverse aperture longitudinally offset from the first aperture. The lag screw assembly includes a lag screw engaged to the second bone segment and a locking sleeve mounted over a proximal portion of the lag screw. The locking sleeve defines a groove aligned with the second aperture. The control member includes a distal portion penetrating the bone segments, an intermediate portion configured to engage the second aperture. and an enlarged head configured to slidably engage the groove. The groove includes a terminus that contacts the head of the control member after a predetermined amount of lateral migration of the lag screw as the fracture collapses.

15 Claims, 7 Drawing Sheets

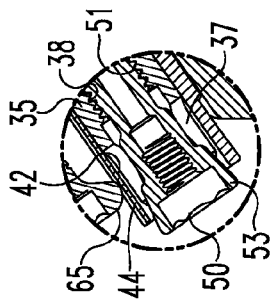
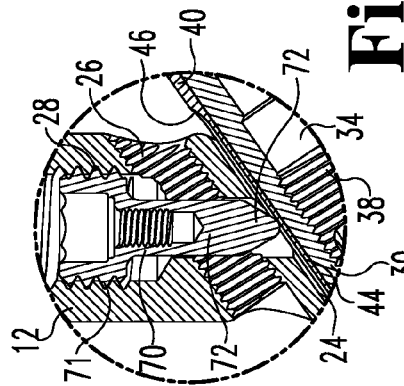
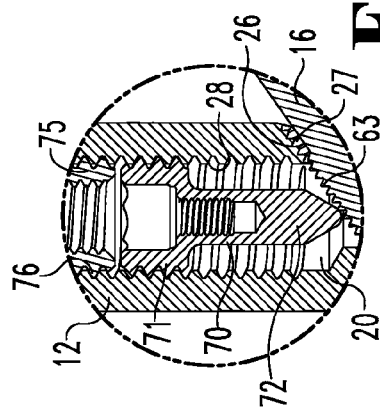
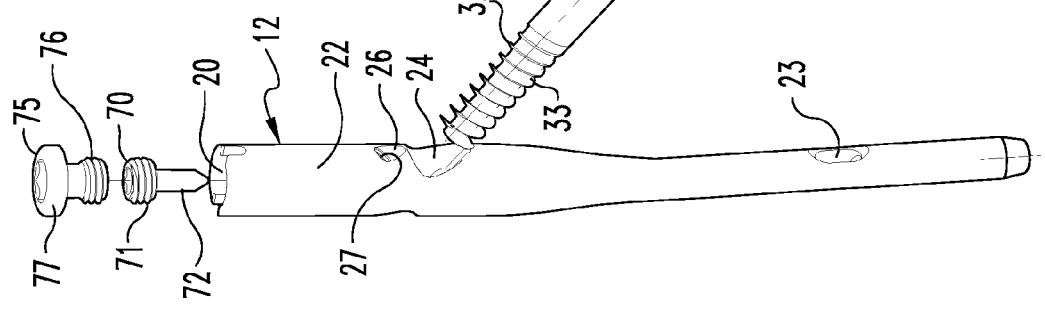

FRACTURE FIXATION APPARATUS

BACKGROUND

The present disclosure relates to orthopaedic devices, and particularly to devices and apparatus for the reduction and fixation of fractures. The disclosed apparatus is useful, for instance, as a compression hip screw to treat femoral fractures occurring at the neck, head or trochanteric region of the femur.

The hip joint is the most heavily loaded and stressed joint of the human body. The joint is essentially a ball and socket joint, with the top of the femur fashioned into the ball that pivots within the cup-shaped acetabulum of the pelvis. The ball or head of the femur is connected to the shaft of the bone by the neck. The neck of the femur is particularly susceptible to fracture under certain loading conditions.

The treatment of such fractures is the same as for any bone—the separated portions must be held together while healing occurs. A variety of devices have been used to successfully treat femoral fractures, with perhaps the most common being the compression hip screw. In one approach, a lag screw extends through an aperture bored through the upper part of the femur and into the broken fragment to hold the broken fragment in proper position during healing. A plate secured to the outside of the shaft of the femur includes a barrel for supporting for the lag screw. A compression screw connects the lag screw to the barrel so that adjusting tension of the compression screw compresses or reduces the femoral fracture as the lag screw is drawn laterally toward the plate. One example of an apparatus of this type is disclosed in U.S. Pat. No. 5,041,116 to Wilson, the disclosure of which is incorporated herein by reference.

Intramedullary devices have also been used successfully to treat femoral fractures. In this approach, a rod or nail is inserted into the medullary canal of the shaft of the femur. Intramedullary rods are frequently used to treat fractures of the lower portions of the femoral shaft. Intramedullary rods are also used to support a lag screw and compression screw for treatment of fractures at the femoral head and neck. The intramedullary rod thus includes one or more transverse apertures to receive the lag screw and compression screw, if present. In some cases, two separate screws are engaged through the intramedullary rod and into the fractured portion of the bone to prevent rotation of the femoral head relative to the remainder of the femur. An example of a device of this type is disclosed in U.S. Pat. No. 5,562,666 to Brumfield, the disclosure of which is incorporated herein by reference.

One problem associated with many lag screw systems is excessive lateral collapse and/or back-out of the lag screw. In some cases, after the fixation device has been implanted the fracture will collapse, meaning the femoral head shifts laterally toward the femoral shaft. If this lateral shift is great enough, the lag screw can extend significantly from the femur, which can lead to patient discomfort and in more extreme cases disengagement of the lag screw from the fixation plate or intramedullary rod. Excessive lateral collapse may also lead to rotation of the fractured femoral head relative to the remainder of the bone, which can compromise proper healing. In these cases, revision surgery may be required.

There is a need for a fracture fixation and reduction apparatus that imposes a limit on lateral collapse of the fracture as well as on the lateral movement of the lag screw.

SUMMARY

In response to this need, the present invention contemplates an apparatus for treating a bone fracture comprises a stabilizing member configured to engage a first bone segment of the fractured bone, the stabilizing member defining a first transverse aperture and a second transverse aperture offset from the first transverse aperture longitudinally along the length of the stabilizing member. The apparatus further comprises an elongated lag screw assembly having a distal portion configured to engage a second bone segment of the fractured bone and a proximal portion configured to slidably extend through the first transverse aperture. The proximal portion defines an elongated groove.

In one feature, the apparatus includes a control member having an elongated shank with a portion configured to engage the second transverse aperture of the stabilizing member and a proximal head that is enlarged relative to the shank. The proximal head is configured to slidably engage the elongated groove when the lag screw assembly extends through the first transverse aperture and the control member extends through the second transverse aperture. This engagement controls or prevents rotation of the lag screw assembly relative to the stabilizing member.

In a further aspect, the groove includes a terminus that is configured to abut the proximal head of the control member after the lag screw assembly has migrated laterally a predetermined distance. The control member thus controls or limits the amount of lateral movement of the lag screw assembly, which ultimately limits the amount of collapse of the fracture.

In certain embodiments, the lag screw assembly includes a lag screw including the distal portion and the proximal portion, and a cylindrical sleeve sized to rotatably fit over the lag screw at the proximal portion, the sleeve defining the elongated groove. A clamping element may be provided for clamping the cylindrical sleeve to the proximal portion of the elongated shank against relative rotation and longitudinal movement. In one embodiment, the clamping element includes a radially expandable segment at the proximal portion of the lag screw within the cylindrical sleeve and an expander element configured to expand the radially expandable segment into clamping engagement with the cylindrical sleeve.

In another embodiment the clamping element includes a castellated segment at the proximal portion of the cylindrical sleeve, at least two notches defined in the proximal portion of the lag screw assembly, and an element including at least two prongs configured for simultaneous mating engagement with the castellated segment of the cylindrical sleeve and the at least two notches of the lag screw assembly.

In another feature, the stabilizing member defines a longitudinal bore therethrough intersecting the first transverse aperture, and includes a locking element configured to engage the lag screw assembly and the longitudinal bore. In certain embodiments in which the first transverse aperture is longitudinally distal the second transverse aperture, the locking element may include opposite prongs defining a slot therebetween, the slot being configured to receive the elongated shank of the control member extending through the second transverse aperture while the opposite prongs engage the lag screw assembly. A capture element may be disposed within the longitudinal bore to capture the locking element within the bore.

The present invention further contemplates an apparatus for treating a bone fracture comprising a stabilizing member configured to engage a first bone segment of the fractured bone, the stabilizing member defining a first transverse aperture and a second transverse aperture offset from the first transverse aperture longitudinally along the length of the stabilizing member, the second transverse aperture having an aperture diameter. The apparatus further comprises an elongated lag screw assembly having a distal portion configured to engage a second bone segment of the fractured bone and a proximal portion configured to slidably extend through the first transverse aperture. A control member is provided having a distal portion configured to penetrate the second bone segment, an intermediate elongated shank having a portion configured to extend through the second transverse aperture of the stabilizing member and a proximal head having a diameter greater than the aperture diameter of the second transverse aperture. In this embodiment, the second transverse aperture is offset from the first transverse aperture by a distance slightly less than half the diameter of the proximal head. The lag screw assembly and control member are thus offset from each other within the fractured bone segment to prevent rotation of the bone segment.

A method for treating a bone fracture is provided that comprises introducing a stabilizing member into a first bone segment of the fractured bone, introducing a lag screw transversely through the stabilizing member, through the first bone segment, across the fracture and into the second bone segment of the fractured bone, and engaging a control member between the stabilizing member and the lag screw to permit limited lateral movement of the lag screw relative to the stabilizing member as the fracture collapses. The method may further comprise engaging the control member between the stabilizing member and the lag screw to prevent rotation of the lag screw relative to the stabilizing member.

One object of the present invention is to provide a fracture fixation apparatus that adequately addresses fracture collapse. More particularly, the object is to control or prevent lateral movement of the lag screw to thereby control or prevent fracture collapse. A further object is to control or prevent rotation of the lag screw relative to a stabilizing member. Yet another object is to control or prevent rotation between the fractured bone segments.

DESCRIPTION OF THE FIGURES

FIG. 2 is an exploded perspective view of one embodiment of the fracture fixation apparatus disclosed herein.

FIG. 6 is an enlarged view of a portion labeled 6 of the apparatus shown in FIG. 3.

FIG. 7 is an enlarged view of the portion labeled 7 of the apparatus shown in FIG. 3.

FIG. 8 is an enlarged view of an alternative configuration of the portion labeled 7 in FIG. 3.

DESCRIPTION OF THE EMBODIMENTS

Figure 1:
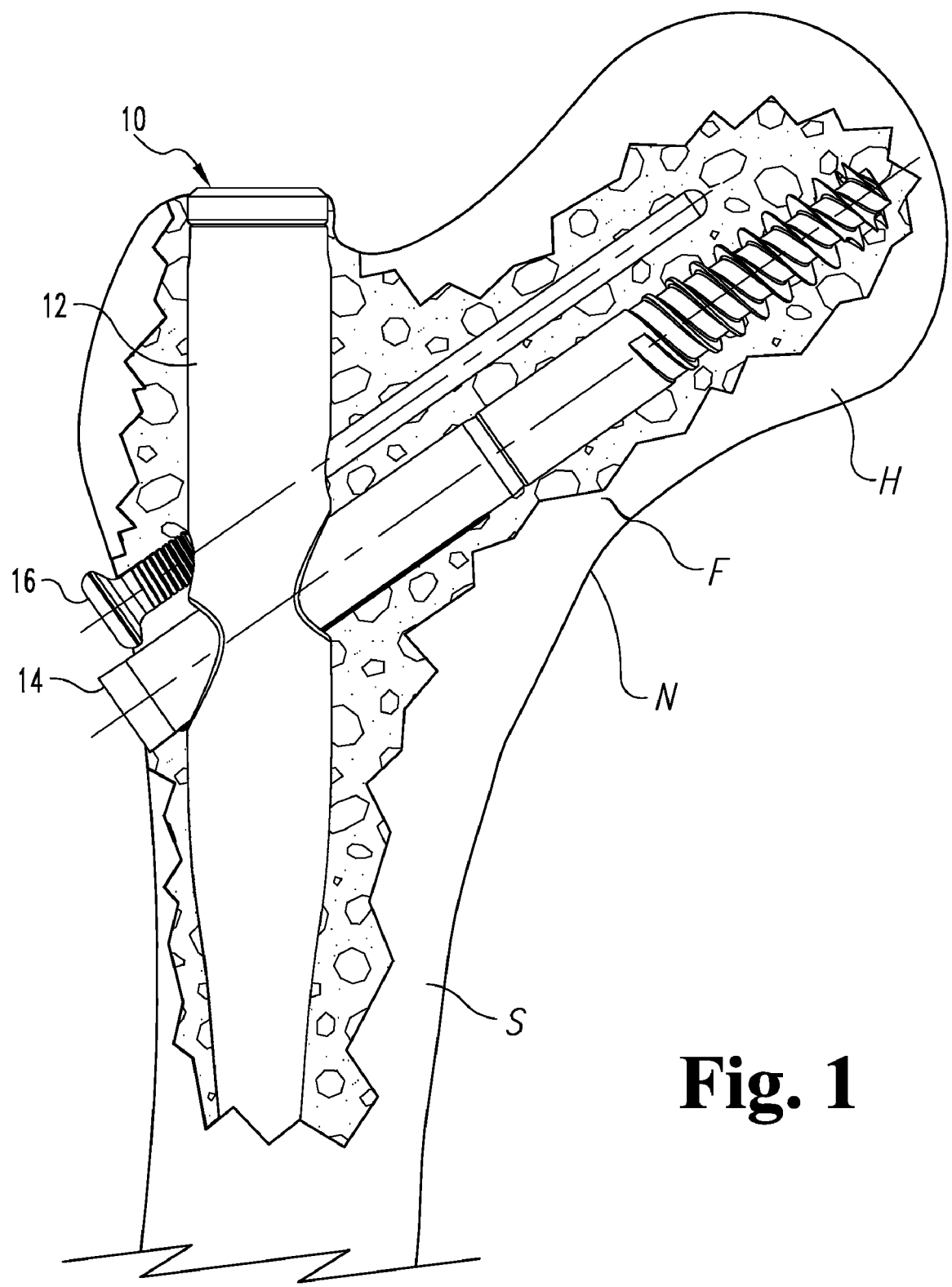
FIG. 1 is a representation of the upper portion of the femur with one embodiment of the fracture fixation apparatus disclosed herein engaged within the femur to fix and reduce a femoral fracture.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A fracture fixation apparatus 10 according to one embodiment is shown in FIG. 1 implanted within a femur having a fracture F at the neck N of the bone. The apparatus 10 includes a stabilizing member in the form of an intramedullary rod or nail 12 extending through the medullary canal of the femoral shaft S, a lag screw assembly spanning the fracture F and engaging the femoral head, and a control member 16. As shown in more detail in FIGS. 2-5, the intramedullary rod 12 defines a central bore 20 that extends along substantially the entire length of the body 22. The body 22 may be configured in a known manner to be implanted within the medullary canal of a long bone, such as the femur. For instance, the body may define a distal aperture to receive a transverse screw for fixing the distal end of the rod to the femur.

The rod 12 further defines a pair of apertures near its proximal end, namely a first transverse aperture 24 and a second transverse aperture 26. The second transverse aperture includes internal threads for engaging the control member 16 as described herein. The rod further includes an upper threaded portion 28 within the central bore 20 for engaging a locking post, as also described herein.

The lag screw assembly 14 includes a lag screw 30 having a distal portion 32 configured to engage the head H of the fractured femur, as shown in FIG. 1. Thus, in one embodiment, the distal portion 32 defines bone threads 33 that can be configured in a manner typical for a lag screw. In certain embodiments, the lag screw 30 may define a bore 34 along its entire length. The bore may define an internal driving feature, such as a hex or Torx configuration, for engagement by a driving tool to implant the lag screw in a known manner.

The lag screw further includes a proximal portion 35 that interfaces with the distal portion 32 at a shoulder 36. In one embodiment, the proximal portion 35 has a smaller diameter than the distal portion 32, so the shoulder 36 represents a step between the two portions. At the end of the proximal portion, the lag screw includes a radially expandable segment 37 in one embodiment, with internal threads 38 defined within the bore 34 immediately distally adjacent the expandable segment. The segment 37 and threads 38 form part of a mechanism for locking the components of the lag screw assembly together, as described in more detail herein.

The lag screw assembly 14 further includes an elongated sleeve 40 that is cylindrical and defines a bore 42 therethrough. The bore 42 is sized so that the sleeve 40 fits over the proximal portion 35 of the lag screw 30 but the distal end 43 of the sleeve butts up against the shoulder 36. In other words, the inner diameter of the sleeve bore 42 is greater than the diameter of the lag screw proximal portion but smaller than the diameter of the lag screw distal portion. The sleeve bore is sized to allow the lag screw to freely rotate within the sleeve while the lag screw is threaded into the fractured head H of the femur in the illustrated embodiment. The length of the sleeve is preferably at least equal to the length of the proximal portion 35 of the lag screw measured from the shoulder 36.

In one feature of the lag screw assembly, the sleeve 40 defines a longitudinal outer groove 44 having an open end 45 at the proximal end 47 of the sleeve and a terminus 46 part way along the length of the sleeve. This groove interfaces with the control member 16 as described herein.

Figures 3, 4:
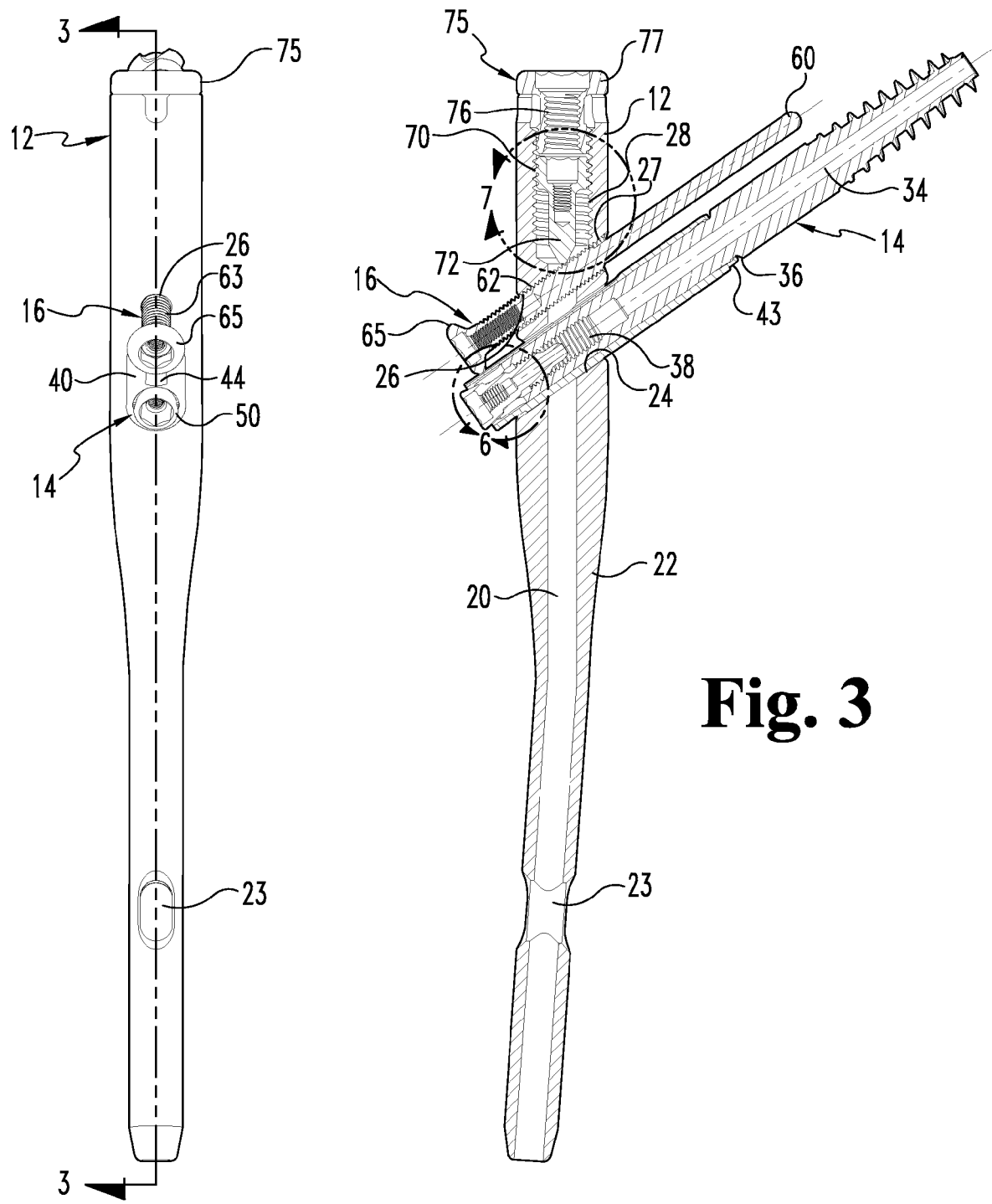
FIG. 3 is a side cross-sectional view of the fracture fixation apparatus shown in FIG. 2, depicted in its assembled configuration.
FIG. 4 is a transverse view of the fracture fixation apparatus shown in FIG. 3.
Figure 5:
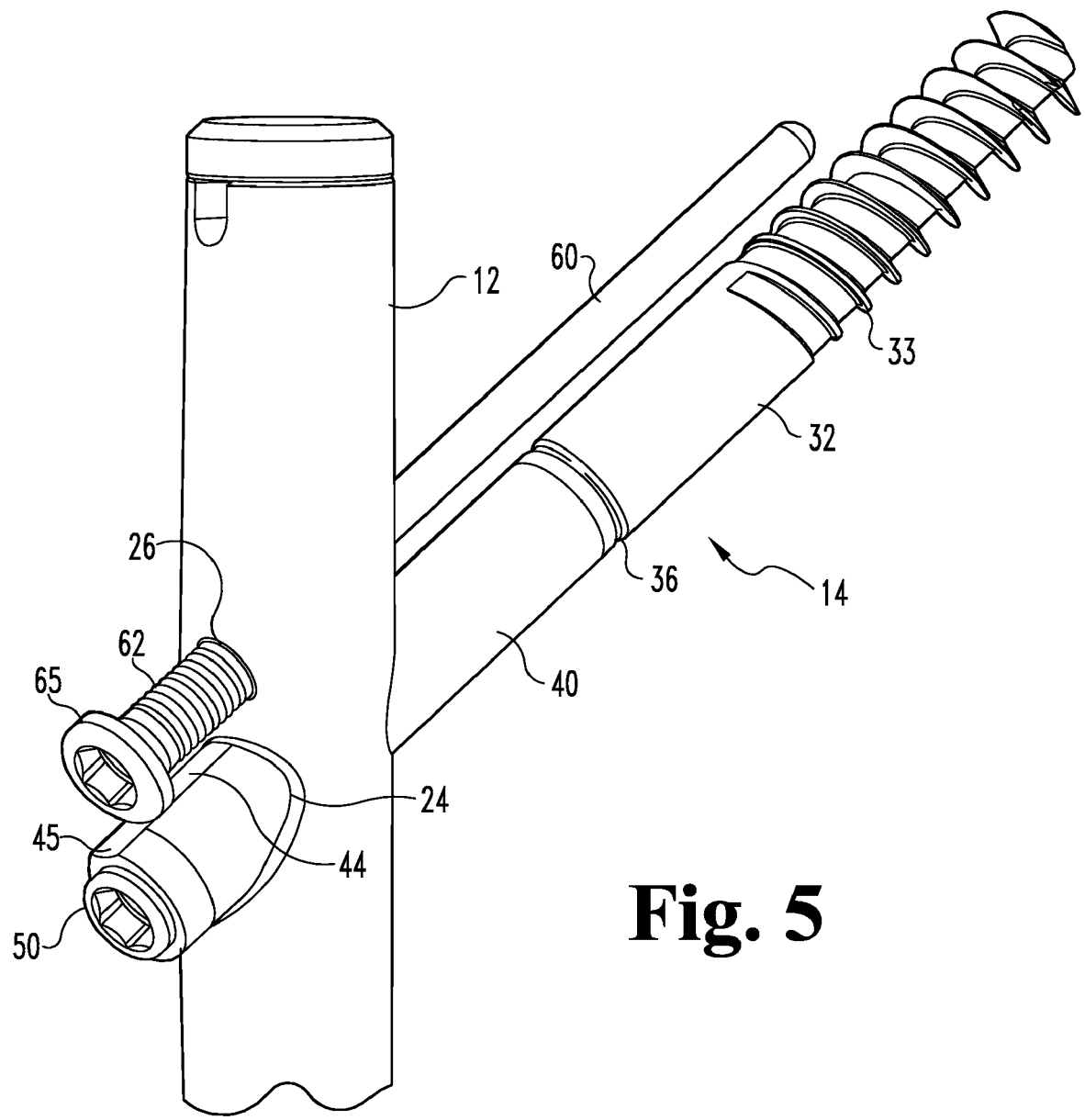
FIG. 5 is an enlarged perspective view of the assembled apparatus shown in FIGS. 3-4.

When the lag screw assembly is constructed, the sleeve 40 is disposed over the proximal portion 35 of the lag screw 30. The lag screw is inserted through the first transverse aperture 20 in the intramedullary rod 12, as shown in FIGS. 2, 3 and 5. The aperture 20 is sized to accept the lag screw and sleeve in a close running fit to allow the lag screw assembly to slide longitudinally through the aperture. As the lag screw is threaded into the femoral head H, it rotates freely within the sleeve 40. When the lag screw 30 has been fully threaded into the fractured bone segment, the sleeve 40 is rotated so that the outer groove 44 is directly aligned with the second transverse aperture 24. In the illustrated embodiment, the second aperture is immediately above or proximal to the first aperture for the lag screw. Thus, the sleeve is rotated until the groove 44 faces upward toward the second aperture.

When the sleeve 40 is properly positioned, it is locked to the lag screw. In one embodiment, the lag screw assembly 14 further includes a locking screw 50 having a threaded end 51 and a conical head 53. The threaded end 51 is configured to engage the internal threads 38 at the end of the proximal portion 35 of the lag screw. The locking screw 50 thus extends through the radially expandable segment 37 of the lag screw and into engagement with the threads 38. As the locking screw is threaded further into the lag screw, the conical head 53 contacts the radially expandable segment, as shown in the enlarged view of FIG. 6. The conical head increases in diameter from a diameter smaller than the un-expanded diameter of the segment 37 to a diameter that is larger than that of the segment. Thus, as the locking screw 50 is advanced, the larger diameter of the conical head 53 bears against the segment 37, forcing it radially outward into contact with the inner surface of the bore 42 of the locking sleeve 40. This radial expansion thus forms a friction fit to lock the sleeve 40 against movement relative to the lag screw 30.

It can also be appreciated that threading the locking screw into the lag screw will tend to pull the lag screw into the locking sleeve until the distal end 43 of the locking sleeve bears against the shoulder 36 of the lag screw. The locking screw 50 thus further acts to compress and clamp the sleeve between the locking screw and the lag screw shoulder. The locking sleeve and lag screw are thus firmly locked together so that the two components move or are prevented from moving as one. The head 53 preferably incorporates a driving feature, such as an internal hex or Torx configuration for engagement by a driving tool to implant the thread the locking screw into the radially expandable segment.

The fracture fixation apparatus 10 further contemplates means for preventing excessive collapse of the fracture F and excessive lateral movement of the lag screw relative to the femoral shaft S. In particular, the apparatus includes a control member 16 that engages both the intramedullary rod 12 and the lag screw 14 in a manner that prevents rotation of the lag screw (and consequently the fractured bone segment) while also restricting lateral movement. The control member 16 includes a non-threaded distal portion 60 that is configured to penetrate the fractured bone segment, as shown in FIG. 1. Thus, the distal portion 60 may be in the form of an orthopaedic nail. The member further includes an intermediate portion 62 that includes outer threads 63. The threads 63 are configured to mate with the internal threads 27 of the second transverse aperture 24 in the intramedullary rod 12 when the control member extends through that aperture. The member terminates in a proximal head 65 that is sized to prevent passage of the head through the second transverse aperture. The head 65 is, however, sized to slidingly engage the groove 44 in the locking sleeve 40 of the lag screw assembly, as best seen in the enlarged view of FIG. 5.

Preferably the groove 44 is defined at a radius that is substantially equal to the radius of the head 65. The depth of the groove is sufficient to capture the head and prevent its dislodgement when the fixation apparatus is under load. In a specific embodiment, the head has a diameter of about 15 mm and a radius of about 7.5 mm. The groove 44 is thus formed at a radius of about 7.5 mm at a depth of about 0.4 mm, subtending an angle of about 40-50°.

With the locking sleeve 40 properly oriented, the control member is passed through the second transverse bore until the threads 63 engage the internal threads 27. A driving feature is preferably incorporated into the head 65, such as an internal hex or Torx configuration for engagement by an appropriate driving tool.

As the control member 16 is threaded into the intramedullary rod 12, the head 65 rotates and slides along the groove 44. It can be appreciated that as the control member 16 is advanced through the second transverse aperture 26 the distal portion 60 is extending essentially parallel to the lag screw 30 into the fractured bone segment. This placement of the control member relative to the lag screw within the fractured femoral head H, for example, prevents the head H from rotating about the longitudinal axis of the lag screw relative to the remainder of the femur. Any torque that may be exerted on the femoral head H that might otherwise cause the fractured segment to rotate is absorbed by the offset lag screw and control member.

The fixation apparatus 10 provides greater resistance to fracture segment rotation than prior devices due to the greater offset achieved between the lag screw and control member. In particular, the two transverse apertures 24, 26 are offset by the radius of the proximal head 65 of the control member (less the depth of the groove 44 within which a portion of the head resides). The greater the offset, the greater the torque resistance capability of the construct.

With the control member 16 in place, the proximal head 65 operates to prevent excessive lateral movement of the lag screw assembly 14. As the fracture F collapses, the lag screw moves laterally, essentially moving retrograde through the first transverse aperture 24. The control member 16, and more importantly the proximal head 65, remains stationary due to the threaded engagement between the control member and the intramedullary rod. The locking sleeve 40 and its groove 44 thus slide along the proximal head until the terminus 46 reaches the head. Since the groove 44 ends, the sleeve can no longer travel past the proximal head 65. The lateral movement of the sleeve 40 and consequently the lag screw 30 locked to the sleeve is stopped.

In a specific embodiment, the groove has a length of about 40 mm from the open end 45 to the terminus 46. Thus, the maximum lateral travel permitted by the control member 16 in this embodiment cannot exceed 40 mm. The actual maximum travel depends upon the position of the proximal head 65 relative to the terminus 46 of the groove 44 when the apparatus 10 is implanted, which will typically be less than the length of the groove. One beneficial feature is that this relative travel, and consequently the maximum lateral movement of the lag screw, can be adjusted when the apparatus is implanted by varying the relative position of the head to the groove terminus. The closer the head 65 is to the terminus 46 at the initial implantation, the less lateral travel that is permitted by the control member 16.

In certain embodiments, a locking mechanism may be provided for locking the control member 16 to the intramedullary rod 12. Thus, as shown in FIGS. 2-3 and in the detail view of FIG. 7, a locking post 70 is disposed within the central bore 20 of the intramedullary rod 12. In one embodiment, the locking post includes a threaded end 71 that engages the internal threads 38 of the central bore. An engagement tip 72 projects from the threaded end and is configured to engage the threaded portion 63 of the control member 16. A capture screw 75 may be provided to lock the locking post 70 in position and to prevent its backing out. The capture screw 75 thus includes a threaded end 76 that engages the internal threads 38 of the central bore and bears against the proximal face of the locking post. An enlarged head 75 may be provided to seal against the top of the intramedullary rod 12. A driving feature is preferably provided in the proximal faces of the locking post 70 and capture screw 75 for engagement by a driving tool.

As shown in FIG. 7, the locking post bears against the control member 16 within the second transverse aperture 26. The engagement tip 72 may be conical, as shown in FIG. 7, or may have other configurations that provide a firm grip against the control member. In certain embodiments, the tip 72 may be malleable to conform to the threaded portion 63 of the control member. When fully engaged, the locking post 70 operates to maintain the control member fixed within the transverse aperture 26. The locking post thus prevents back out of the control member 16 which would otherwise thwart a central purpose of the member to restrict lateral movement of the lag screw.

The fracture fixation apparatus 10 is preferably used with both the lag screw 14 and the control member 16. In certain applications, the control member 16 is not necessary to prevent or restrict back out or lateral movement, or even rotation, of the lag screw. In those applications the control member 16 is not used. The locking post 70 may then be threaded more deeply into the internal threads 38 of the central bore until the tip 72 engages the sleeve 40, as shown in FIG. 8, which is itself locked to the lag screw in the manner explained above. In the embodiment shown in FIG. 8, the capture screw may be modified so that the threaded end 76 can be threaded deeper into the central bore 20 to contact the proximal face of the locking post.

Figure 9:
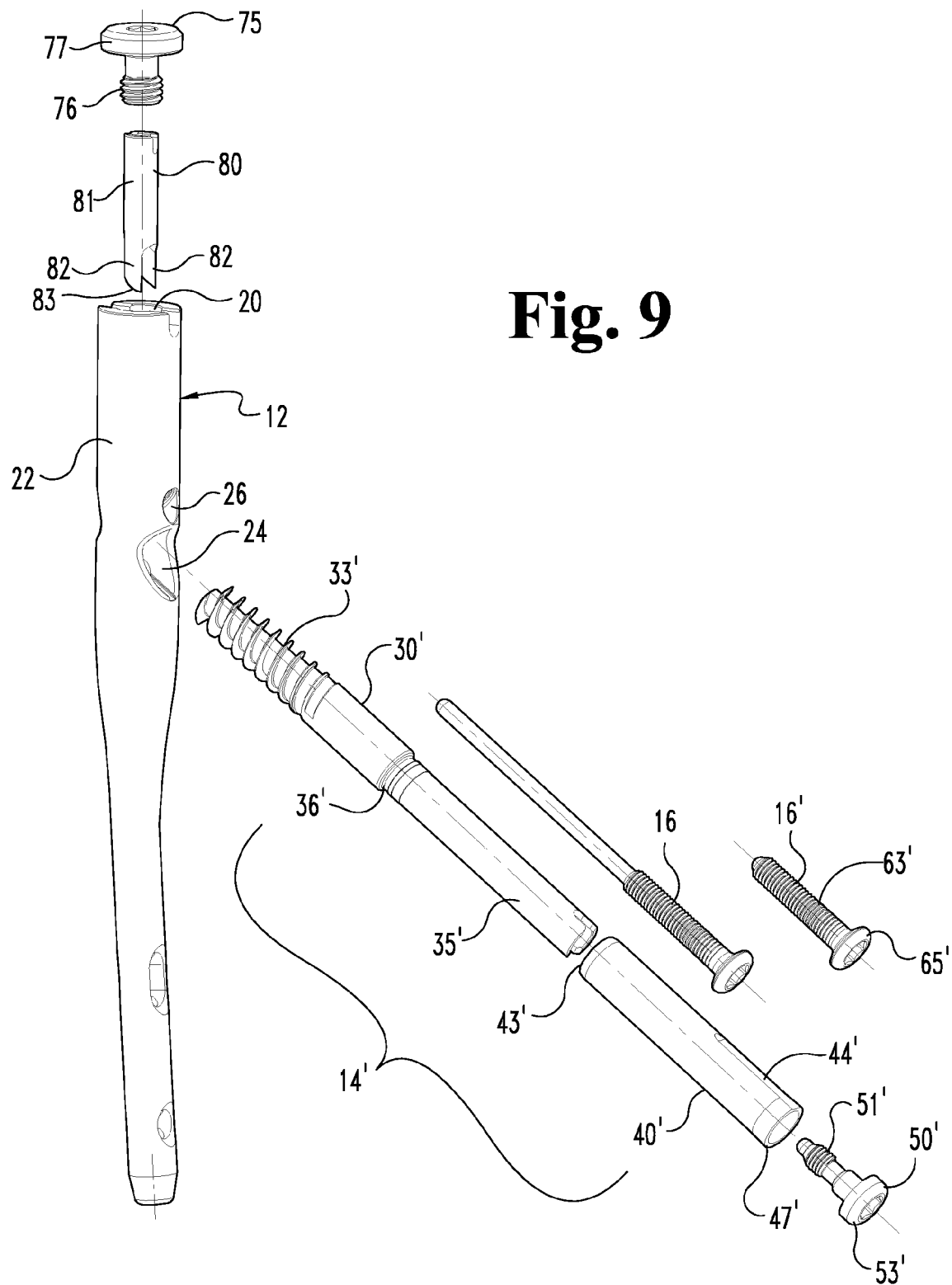
FIG. 9 is an exploded perspective view of an alternative embodiment of the fracture fixation apparatus disclosed herein.
Figure 10:
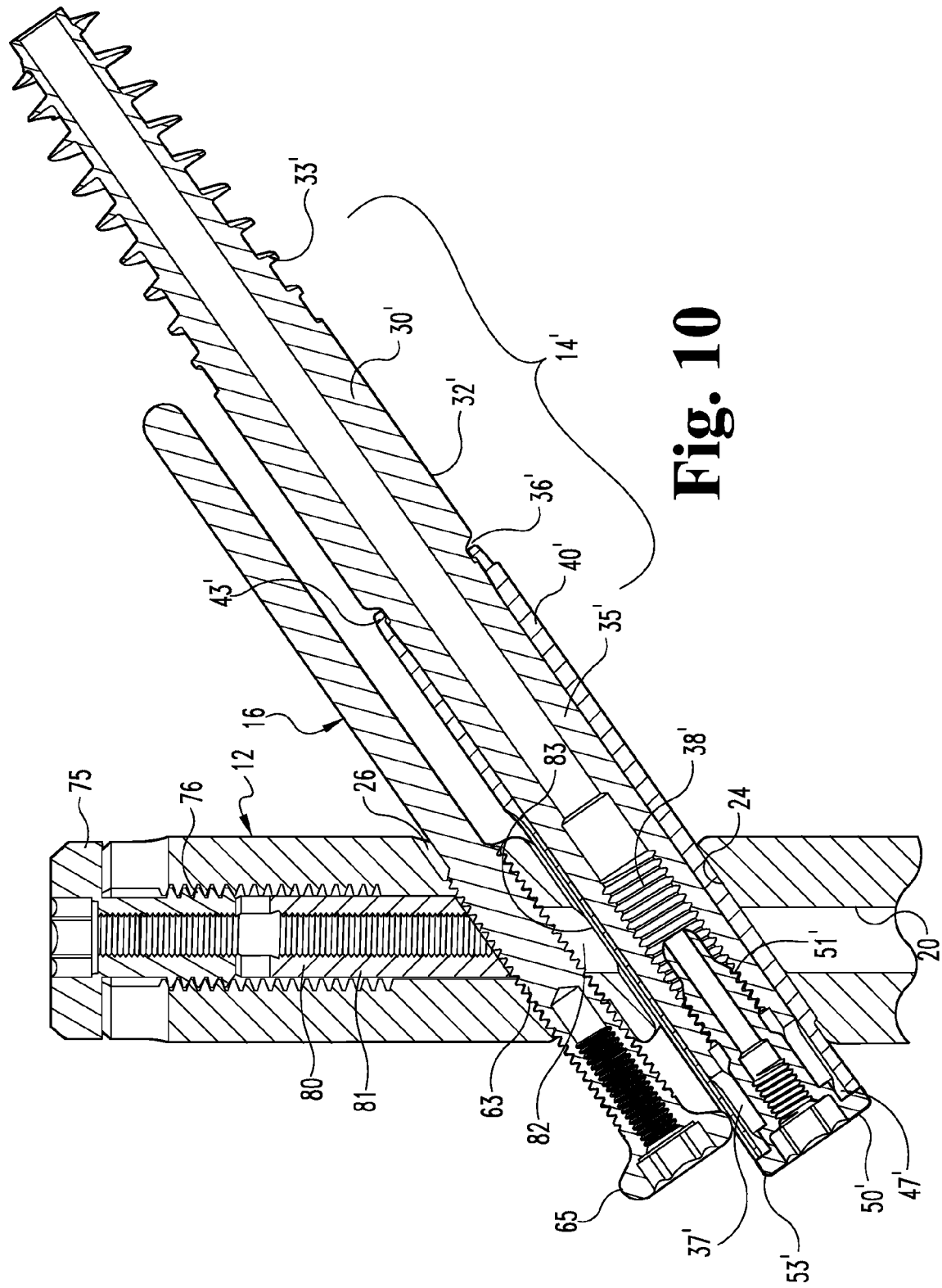
FIG. 10 is an enlarged cross-sectional view of the embodiment shown in FIG. 9.

In an alternative embodiment, a locking post 80 may be provided as shown in FIGS. 9-10. In that embodiment, the locking post includes an unthreaded upper tube 81 sized to freely slide within the central bore. The distal end of the tube is formed into opposite prongs 82 that are spaced apart to pass around the threaded portion 63 of the control member 16 disposed within the second transverse aperture 26, as best seen in FIG. 10. The prongs are sized so that the tips 83 of the prongs can bear against the sleeve 40 (or sleeve 40' shown in FIG. 10). The tips 83 are preferably angled to conform to the surface of the locking sleeve. This surface to surface engagement increases the frictional locking capability of the locking post 80 to prevent or significantly restrict the lateral migration of the lag screw assembly.

This alternative embodiment locking post 80 may be particularly useful with the lag screw assembly 14' embodiment shown in FIGS. 9-10. This lag screw assembly 14' includes a modified lag screw 30' that does not incorporate the radially expandable segment 37 of the embodiment shown in FIGS. 2, 6. In addition, the modified lag screw 30' includes a shoulder that is modified to provide a circumferential depression 36' at the interface between the distal portion 32' and proximal portion 35'. The locking sleeve 40' is also modified so that its distal end 43' curves inward to engage the circumferential depression 36', as best seen in FIG. 10.

The modified lag screw assembly 14' also includes a modified locking screw 50'. The locking screw includes a threaded post 51 configured to engage internal threads 38' of the lag screw 30'. The head 53' is configured to bear against the proximal end 47' of the modified locking sleeve 40'. The proximal end 37' of the lag screw 30' is offset from the proximal end 47' of the locking sleeve 40' so that threading the locking screw 50' into the threads 38' allows the locking screw to exert a compressive force against the sleeve. This compression will clamp the sleeve 40' between the depression 36' and the shoulder formed by the distal portion 32' of the lag screw and the head 53' of the locking screw 50' The locking screw thus locks the sleeve 40' to the lag screw 30'. The modified locking post 80 provides further locking force to the sleeve.

Figure 11:
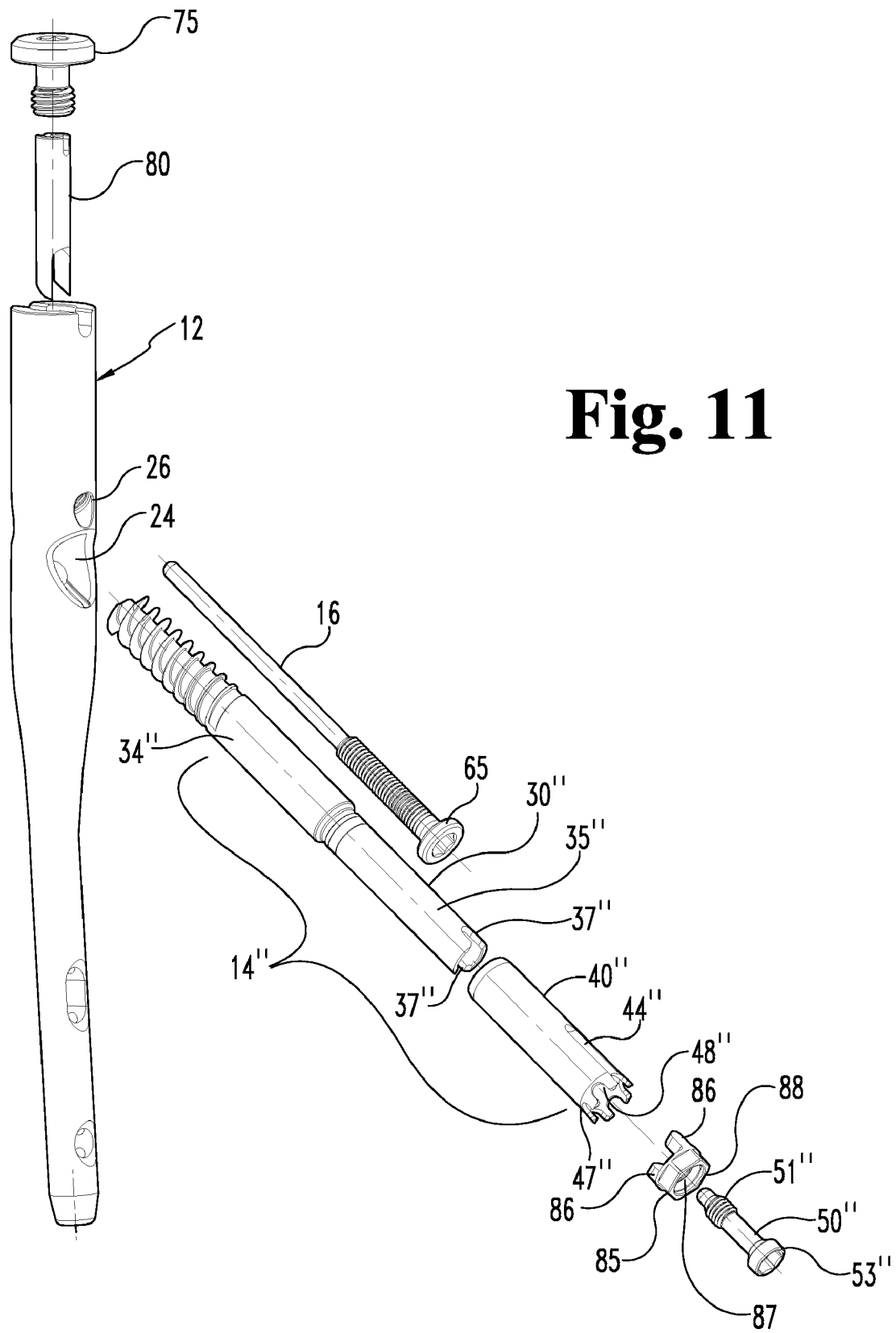
FIG. 11 is an exploded perspective view of a further embodiment of the fracture fixation apparatus disclosed herein.

The engagement between the locking sleeve and the lag screw may be modified as shown in FIG. 11. In particular, the lag screw assembly 14" includes a locking sleeve 40" with a slot 44" that is configured like the other embodiments 40 and 40'. However, the proximal end 47" of the sleeve 40" is castellated to include a series of circumferentially arranged recesses 48". The locking screw 50" is also modified from the prior embodiments to mate with a nut 85. The nut 85 includes at least two prongs 86 that are configured to fit within diametrically opposite recesses 48" in the locking sleeve 40". The nut 85 defines an opening 87 through which the locking screw 50" passes. The head 53" of the screw is contoured to fit within a contoured seat 88 of the nut. The screw further includes a threaded stem 51" that is configured to engage the internal threads of the lag screw, such as threads 38 shown in FIG. 6, in the manner described above.

In this embodiment, the lag screw 30" of the assembly 14" is also modified from the prior embodiments. In particular, the end of the proximal portion 35" is modified to incorporate at least two diametrically opposite notches 37". The notches 37" are adapted to receive the prongs 86 of the nut 85. The lag screw assembly 14" is assembled by sliding the sleeve 40" over the proximal portion 35" of the lag screw 30". As explained above with respect to the embodiment of FIG. 2, the sleeve is oriented so that the groove 44" is aligned with the second transverse aperture 26 of the intramedullary rod 12 for engagement by the control member 16 in the manner described. The lag screw and locking sleeve may be rotated slightly so that the notches 37" align with recesses 48" in the castellated proximal end 47" of the sleeve. The nut may then be positioned over of the two components with the prongs 86 positioned with aligned pairs of notches 37" and recesses 48". The locking screw 50" is then advanced into the threaded end of the lag screw and the head 53" is tightened down into the contoured seat 88 of the nut. Tightening the locking screw 50" not only compresses and clamps the locking sleeve 40" against the distal portion 32" of the lag screw, it also rotationally locks the sleeve and lag screw together by way of the prongs 86. When the head 65 of the control member 16 is engaged within the groove 44", the entire lag screw assembly 14" is locked against rotation relative to the intramedullary rod. The completed assembly thus prevents rotation of the fractured bone segment as well as limits collapse of the fracture and lateral migration of the lag screw.

In certain embodiments, the control member need not engage the fractured bone segment in the manner shown in FIG. 1. In these embodiments, an abbreviated control member 16' may be provided as depicted in FIG. 9. This modified control member only includes the proximal head 65' and the threaded portion 63' adapted to engage the internal threads of the second transverse aperture 26 in the intramedullary rod. This abbreviated control member does not include the elongated distal portion of the prior embodiment (i.e., the distal portion 60 of the control member 16 shown in FIG. 2), so the control member 16' does not operate to prevent rotation of the fractured bone segment about the axis of the lag screw. However, this embodiment of the control member 16' is acceptable for fracture fixation where there is little risk of fracture rotation.

Alternative embodiments are contemplated that can achieve the functional benefits of the embodiments just described. For instance, in the illustrated embodiments, the groove 44/44'/44" in the corresponding locking sleeve 40/40'/40" has a length sized to permit a limited amount of lateral migration of the lag screw during fracture collapse. In alternative embodiments, the length of the groove can be made much shorter to reduce or even eliminate the lateral movement of the lag screw.

The embodiments illustrated and described herein are especially adapted for use in fixation of fractures of the femoral head H, as shown in FIG. 1. Thus, each of the components is sized for implantation within the proximal portion of the femur. Of course, the intramedullary rod 12, lag screw 40/40'/40" and control member 16/16' can be provided in diameters and lengths suitable for the patient's anatomy. The fracture fixation apparatus 10 may be adapted for fixation of fractures other than of the femur. In other applications, the intramedullary rod 12 may be replaced by a bone plate, for instance, that incorporates the first and second transverse apertures 24, 26. Appropriate changes to the geometry and dimensions of the lag screw assembly and control member may also be made for these other fracture fixation applications, while retaining the anti-rotation and anti-lateral migration features provided by the apparatus of the embodiments disclosed herein.

There are many advantages arising from the various features of each of the embodiments described herein. It will be noted that alternative embodiments of the assembly may not include all of the features described yet still benefit from at least some of the advantages of such features. Those of ordinary skill in the art may readily devise their own implementations of the assembly that incorporates one or more of the features and fall within the spirit and scope of the present invention as defined by the appended claims.

What is claimed is:

1. An apparatus for treating a bone fracture, comprising:
a stabilizing member configured to engage a first bone segment of the fractured bone, said stabilizing member including a first transverse aperture structure defining a first transverse aperture and a second transverse aperture structure defining a second transverse aperture offset from said first transverse aperture longitudinally along the length of said stabilizing member;
an elongated lag screw assembly configured to (i) engage a second bone segment of the fractured bone, and (ii) slidably extend through said first transverse aperture of said stabilizing member; and
a control member having (i) an elongated shank with a portion configured to engage said second transverse aperture structure of said stabilizing member, and (ii) a proximal head that is enlarged relative to said shank,
wherein said lag screw assembly includes (i) a lag screw including a distal portion configured to engage said second bone segment of the fractured bone and a proximal portion, and (ii) a cylindrical sleeve sized to rotatably fit over said lag screw at said proximal portion,
wherein said cylindrical sleeve includes an elongated groove structure that defines an elongated groove that is configured to receive said proximal head of said control member therein, and
wherein said proximal head of said control member is configured to slidably engage said elongated groove structure when said lag screw assembly extends through said first transverse aperture and said control member extends through said second transverse aperture.

2. The apparatus of claim 1, wherein:
said distal portion of said lag screw is defined at a diameter greater than said proximal portion so that said lag screw defines a shoulder between said distal and proximal portions; and
said sleeve has a length at least equal to the length of said proximal portion measured from said shoulder.

3. The apparatus of claim 1, wherein said lag screw assembly further includes a clamping assembly configured to clamp said cylindrical sleeve to said proximal portion of said lag screw when said cylindrical sleeve is fit over said lag screw.

4. The apparatus of claim 3, wherein said clamping assembly includes (i) a radially expandable segment at said proximal portion of said lag screw, and (ii) an expander element configured to expand said radially expandable segment into clamping engagement with said cylindrical sleeve when said radially expandable segment is positioned within said cylindrical sleeve.

5. The apparatus of claim 3, wherein said clamping assembly includes:
a castellated segment at a proximal part of said cylindrical sleeve;
at least two notches defined in the proximal portion of said lag screw; and
an element including at least two prongs configured for simultaneous mating engagement with said castellated segment of said cylindrical sleeve and said at least two notches of said lag screw.

6. The apparatus of claim 5, wherein:
said element includes;
a nut including said at least two prongs and defining an opening with a seat; and
a locking screw having a threaded stem adapted to extend through said opening in said nut and a head adapted to sit within said seat of said nut; and
said lag screw defines a bore having a threaded portion configured to engage said threaded stem of said locking screw.

7. The apparatus of claim 1, wherein said stabilizing member includes (i) a longitudinal bore structure defining a longitudinal bore intersecting said first transverse aperture, and (ii) a locking element configured to engage said lag screw assembly and said longitudinal bore structure.

8. The apparatus of claim 7, wherein:
said first transverse aperture is longitudinally distal said second transverse aperture; and
said locking element includes opposite prongs defining a slot therebetween, said slot configured to receive said elongated shank of said control member extending through said second transverse aperture while said opposite prongs engage said lag screw.

9. The apparatus of claim 8, further comprising a capture element disposed within said longitudinal bore and configured to capture said locking element within said bore.

10. The apparatus of claim 7, wherein:
said longitudinal bore of said stabilizing member intersects said second transverse aperture,
said longitudinal bore structure defines internal threads; and
said locking element includes a threaded end adapted to engage said internal threads, and an engagement tip arranged to bear against either said control member within said second transverse aperture or said lag screw within said first transverse aperture.

11. The apparatus of claim 1, wherein said second transverse aperture structure and said portion of said elongated shank of said control member are positioned in threaded engagement with each other.

12. The apparatus of claim 1, wherein said proximal head and said elongated groove are defined at substantially the same radius.

13. The apparatus of claim 1, wherein said elongated groove is open at a proximal end of said elongated lag screw and defines a terminus distally offset from said proximal end, said terminus configured to prevent relative movement of said proximal head distal of said terminus.

14. The apparatus of claim 1, wherein said control member further includes a bone engagement portion extending from said elongated shank and configured to penetrate said second bone segment.

15. An apparatus for treating a bone fracture comprising:
a stabilizing member configured to engage a first bone segment of the fractured bone, said stabilizing member defining a first transverse aperture and a second transverse aperture offset from said first transverse aperture longitudinally along the length of said stabilizing member, said second transverse aperture having an aperture diameter;
an elongated lag screw assembly having a distal portion configured to engage a second bone segment of the fractured bone and a proximal portion configured to slidably extend through said first transverse aperture; and
a control member having a distal portion configured to penetrate said second bone segment, an intermediate elongated shank having a portion configured to extend through said second transverse aperture of said stabilizing member and a proximal head having a diameter greater than said aperture diameter of said second transverse aperture,
wherein said second transverse aperture is offset from said first transverse aperture by a distance slightly less than half said diameter of said proximal head.

* * * * *

UNITED STATES PATENT AND TRADEMARK OFFICE
CERTIFICATE OF CORRECTION

PATENT NO. : 8,100,911 B2
APPLICATION NO. : 12/164475
DATED : January 24, 2012
INVENTOR(S) : Ken Yamazaki et al.

It is certified that error appears in the above-identified patent and that said Letters Patent is hereby corrected as shown below:

Column 1,
Line 67, after "fracture" insert --that--

Column 2,
Line 52, after "distal" insert --to--

Column 5,
Lines 3-4, replace "first transverse aperture 20" with --first transverse aperture 24--

Column 5,
Line 5, replace "apterture 20" with --aperture 24--

Column 5,
Line 45, after "thread" insert --of--

Column 5,
Lines 60-61, replace "the second transverse aperture 24" with --the second transverse aperture 26--

Column 8,
Line 7, after "50'" insert --.--

Column 8,
Line 42, after "over" delete "of"

Column 10,
Line 33, replace "includes;" with --includes:--

Signed and Sealed this
Twelfth Day of March, 2013

Teresa Stanek Rea
*Acting Director of the United States Patent and Trademark Office*